US00PP14534P29

(12) United States Plant Patent
Wood

(10) Patent No.: US PP14,534 P2
(45) Date of Patent: Feb. 17, 2004

(54) ANTIRRHINUM PLANT NAMED 'DELA 1'

(50) Latin Name: *Antirrhinum majus*
Varietal Denomination: Dela 1

(75) Inventor: Peter Wood, Wisbech (GB)

(73) Assignee: R. Delamone Ltd., Wisbech (GB)

( * ) Notice: Subject to any disclaimer, the term of this patent is extended or adjusted under 35 U.S.C. 154(b) by 0 days.

(21) Appl. No.: 10/396,573

(22) Filed: Mar. 25, 2003

(51) Int. Cl.[7] ..... A01H 5/00
(52) U.S. Cl. ..... Plt./322
(58) Field of Search ..... Plt./322

*Primary Examiner*—Kent Bell
(74) *Attorney, Agent, or Firm*—C. A. Whealy

(57) ABSTRACT

A new and distinct cultivar of Antirrhinum plant named 'Dela 1', characterized by its upright and mounded plant habit; freely branching growth habit; grayed green and white variegated foliage; and red purple-colored flowers.

1 Drawing Sheet

Botanical classification/cultivar denomination: *Antirrhinum majus* cultivar Dela 1.

BACKGROUND OF THE INVENTION

The present Invention relates to a new and distinct cultivar of Antirrhinum plant, botanically known as *Antirrhinum majus,* and hereinafter referred to by the name 'Dela 1'.

The new Antirrhinum is a product of a planned breeding program conducted by the Inventor in Wisbech, United Kingdom. The objective of the breeding program is to develop new vigorous Antirrhinum cultivars that have variegated foliage and numerous flowers with attractive coloration.

The new Impatiens originated from a cross-pollination made by the Inventor in 1998 of two unidentified proprietary seedling selections of *Antirrhinum majus,* not patented. The cultivar Dela 1 was discovered and selected by the Inventor as a flowering plant within the progeny of the stated cross-pollination in a controlled environment in Wisbech, United Kingdom.

Asexual reproduction of the new cultivar by cuttings taken in Wisbech, United Kingdom since November, 2000, has shown that the unique features of this new Antirrhinum are stable and reproduced true to type in successive generations.

SUMMARY OF THE INVENTION

The following traits have been repeatedly observed and are determined to be the unique characteristics of 'Dela 1'. These characteristics in combination distinguish 'Dela 1' as a new and distinct Antirrhinum cultivar:

1. Upright and mounded plant habit.
2. Freely branching growth habit.
3. Grayed green and white variegated foliage.
4. Red purple-colored flowers.

Plants of the new Antirrhinum differ primarily from plants of the parent selections in foliage and flower coloration.

Plants of the new Antirrhinum can be compared to plants of the cultivar Lapin, disclosed in U.S. Plant Pat. No. 10,005. In side-by-side comparisons conducted in Wisbech, United Kingdom, plants of the new Antirrhinum differed from plants of the cultivar Lapin in the following characteristics:

1. Plants of the new Antirrhinum were more upright than plants of the cultivar Lapin.
2. Plants of the new Antirrhinum had grayed green and white variegated leaves whereas plants of the cultivar Lapin had solid green-colored leaves.
3. Flower color of plants of the new Antirrhinum was darker red purple than flower color of plants of the cultivar Lapin.

BRIEF DESCRIPTION OF THE PHOTOGRAPHS

The accompanying colored photographs illustrate the overall appearance of the new Antirrhinum, showing the colors as true as it is reasonably possible to obtain in colored reproductions of this type. Colors in the photographs may differ from the color values cited in the detailed botanical description which accurately describe the colors of the new Antirrhinum.

The photograph at the top of the sheet comprises a side perspective view of a typical flowering plant of 'Dela 1'.

The photograph at the bottom of the sheet comprises a close-up view of typical flowers of 'Dela 1'.

DETAILED BOTANICAL DESCRIPTION

The cultivar Dela 1 has not been observed under all possible environmental conditions. The phenotype may vary somewhat with variations in environment such as temperature and light intensity without, however, any variance in genotype.

The aforementioned photographs and following observations and measurements describe plants grown during the summer in Wisbech, United Kingdom, under commercial practice in a glass-covered greenhouse with day temperatures about 18° C. and night temperatures about 12° C. Rooted young plants were planted in containers and had been growing for about four months when the photographs and the description were taken.

In the following description, color references are made to The Royal Horticultural Society Colour Chart, 1995 Edition, except where general terms of ordinary dictionary significance are used.

Botanical classification: *Antirrhinum majus* cultivar Dela 1.

Parentage:

*Female parent.*—Unidentified proprietary seedling selection of *Antirrhinum majus,* not patented.

*Male parent.*—Unidentified proprietary seedling selection of *Antirrhinum majus,* not patented.

Propagation:

*Type.*—Cuttings.

*Time to develop roots.*—About 28 days at 20° C.

*Root description.*—Fibrous; whitish in color.

Plant description:

*General appearance.*—Upright and mounded plant habit; moderately vigorous. Freely branching growth habit with lateral branches potentially forming at every node.

*Plant height.*—About 30 cm.

*Plant diameter or spread.*—About 25 cm.

*Flowering stem diameter.*—About 2 to 3 mm.

*Flowering stem internode length.*—About 5 to 12 mm.

*Flowering stem texture.*—Smooth, glabrous.

*Flowering stem color.*—46B.

*Foliage description.*—Arrangement: Opposite, simple. Length: About 4 to 6 cm. Width: About 7 to 23 mm. Shape: Elliptic. Apex: Acute. Base: Attenuate. Margin: Entire. Texture, upper and lower surfaces: Smooth, glabrous. Venation pattern: Pinnate. Color: Developing and fully expanded leaves, upper surface: Center, 191A; white margins, 155A in color and about 1 to 2 mm in width. Developing and fully expanded leaves, lower surface: Center, 191A to 191B; white margins, 155A in color and about 1 to 2 mm in width. Petiole: Length: About 3 to 12 mm. Diameter: About 1 mm. Texture, upper and lower surfaces: Smooth, glabrous. Color, upper and lower surfaces: 191A.

Flower description:

*Flower type and flowering habit.*—Single bi-labiate flowers arranged on terminal racemes; flowers opposite. Usually about 5 to 15 open flowers and flower buds per raceme. Flowers face outwardly. Flowers self-cleaning. Flowers not fragrant.

*Flower longevity.*—Flowers last about 2 to 10 days on the plant.

*Natural flowering season.*—Flowering is intermittent to continuous from May until November in Wisbech, United Kingdom.

*Flower diameter.*—About 3.2 to 3.7 cm.

*Flower depth (height).*—About 4.5 to 5 cm.

*Flower buds.*—Length: About 1.5 to 2.5 cm. Diameter: About 1 to 1.5 cm. Shape: Oblong. Color (sepals, lower surface): 191A with white, 155A, margins.

*Corolla.*—Shape: Bilabiate; lower lip with palate. Lobe apices: Rounded; undulating. Lobe margin: Entire. Length, upper lip: About 4.5 to 5 cm. Length, lower lip: About 3.5 to 4 cm. Width, upper lip: About 3.7 cm. Width, lower lip: About 3.2 cm. Texture, upper and lower surfaces of lobes: Satiny. Lobe color: Upper and lower lips, upper surface: 63B; color becoming closer to 62C with development. Upper and lower lips, lower surface: 63C. Palate: 9A; color becoming closer to 3A with development.

*Sepals.*—Quantity/arrangement: Five per flower; fused at base. Shape: Ovate. Apex: Acute. Margin: Entire. Texture, upper and lower surfaces: Densely pubescent. Color, upper and lower surfaces: 191A with white, 155A, margins.

*Pedicels.*—Length: About 3 to 6 mm. Diameter: Less than 1 mm. Strength: Strong; flexible. Angle: Erect. Color: 138C.

*Reproductive organs.*—Androecium: Stamen quantity: Four per flower. Filament length: About 2 to 2.4 cm. Filament color: 62C. Anther length: About 2 mm. Anther color: 16C. Pollen color: 22C. Gynoecium: Pistil quantity: One per flower. Style length: About 2 cm. Style color: 62C. Stigma color: 151A. Ovary length: About 3 to 6 mm. Ovary color: 154D.

*Seeds/fruits.*—Seed and fruit development has not been observed.

Disease/pest resistance: Plants of the new Antirrhinum have not been observed to be resistant to pathogens and pests common to Antirrhinum.

Temperature tolerance: Plants of the new Antirrhinum have been observed to tolerate temperatures from 0 to 35° C.

It is claimed:

1. A new and distinct cultivar of Antirrhinum plant named 'Dela 1', as illustrated and described.

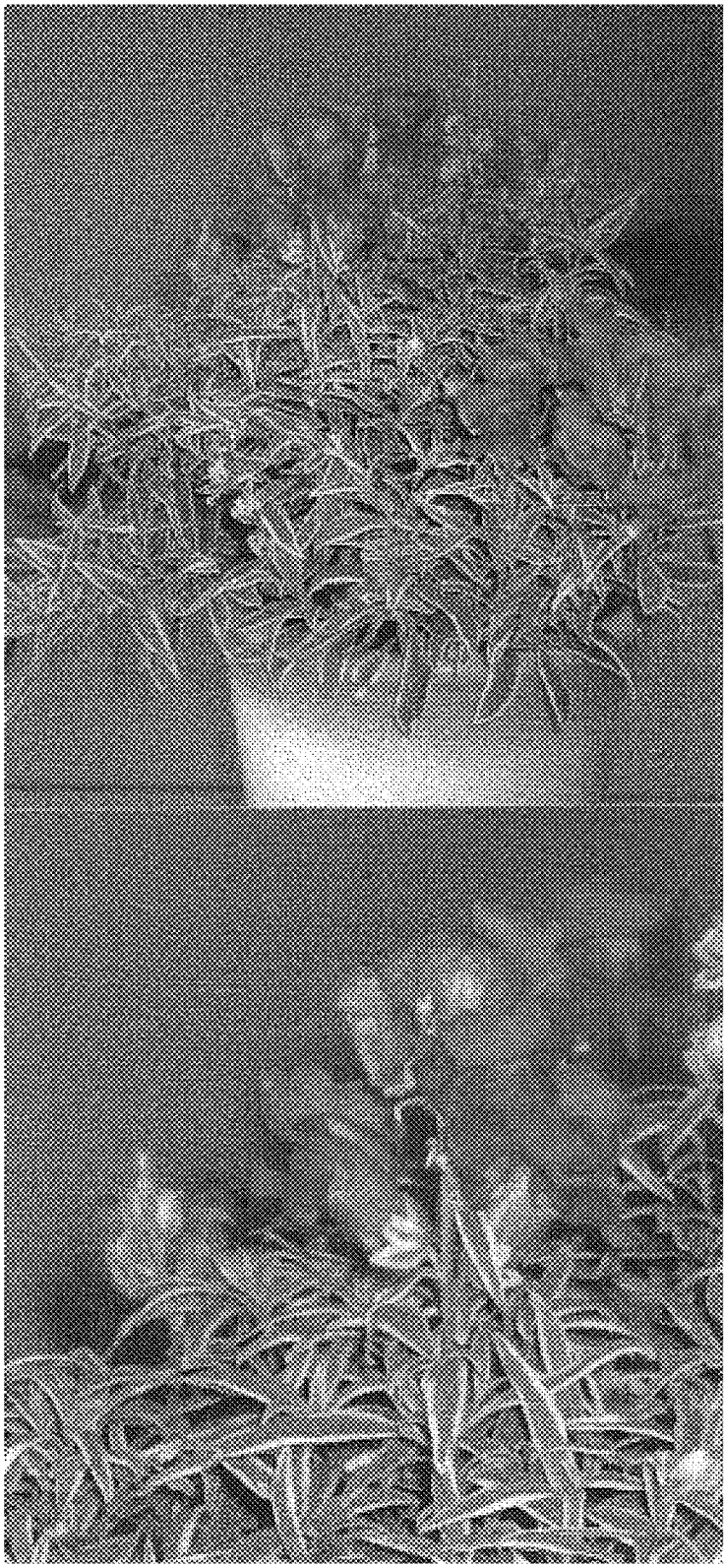

* * * * *